United States Patent
Coelho Alves et al.

(10) Patent No.: US 11,908,145 B2
(45) Date of Patent: Feb. 20, 2024

(54) DIGITAL ASSESSMENT OF POSITION OF MOTION TRACKERS ON A PERSON

(71) Applicant: SWORD HEALTH, S.A., Oporto (PT)

(72) Inventors: José Carlos Coelho Alves, Oporto (PT); Márcio Filipe Moutinho Colunas, Oporto (PT); Pedro Henrique Oliveira Santos, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 18/128,205

(22) Filed: Mar. 29, 2023

(65) Prior Publication Data

US 2023/0281831 A1 Sep. 7, 2023

Related U.S. Application Data

(63) Continuation of application No. PCT/EP2022/057901, filed on Mar. 25, 2022.

(30) Foreign Application Priority Data

Mar. 30, 2021 (EP) .................................. 21398004

(51) Int. Cl.
*G06T 7/73* (2017.01)
*G06T 7/246* (2017.01)
*G06V 10/141* (2022.01)

(52) U.S. Cl.
CPC ............... *G06T 7/246* (2017.01); *G06T 7/73* (2017.01); *G06V 10/141* (2022.01); *G06T 2207/10024* (2013.01); *G06T 2207/20044* (2013.01)

(58) Field of Classification Search
CPC G06T 7/246; G06T 7/248; G06T 7/70; G06T 7/73; G06T 7/74; G06T 2207/10152; G06T 2207/30204; G06V 10/141; G06V 10/245; G06F 3/011; A61B 90/39; A61B 2090/3975; A61B 2090/3983
See application file for complete search history.

(56) References Cited

U.S. PATENT DOCUMENTS

| | | | |
|---|---|---|---|
| 11,172,850 B2 | 11/2021 | Persidsky et al. | |
| 2020/0037942 A1 | 2/2020 | Howard | |
| 2020/0146594 A1 | 5/2020 | Gong et al. | |
| 2020/0371584 A1 | 11/2020 | Zhao et al. | |
| 2021/0219925 A1 | 7/2021 | Au et al. | |
| 2023/0043103 A1* | 2/2023 | Pritchett et al. | A61B 5/1127 |

FOREIGN PATENT DOCUMENTS

| | | |
|---|---|---|
| CN | 110381286 A | 10/2019 |
| CN | 110853620 A | 2/2020 |
| CN | 107016996 B | 11/2020 |
| EP | 3751531 A1 | 12/2020 |
| EP | 3792928 A1 | 3/2021 |
| GB | 2466714 A | 7/2010 |
| WO | WO-2013070171 A1 | 5/2013 |
| WO | WO-2018121708 A1 | 7/2018 |
| WO | WO-2019243438 A1 | 12/2019 |
| WO | WO-2021048022 A1 | 3/2021 |
| WO | WO-2022167582 A1 | 8/2022 |
| WO | WO-2022207485 A1 | 10/2022 |

OTHER PUBLICATIONS

U.S. Appl. No. 18/128,197 Non-Final Office Action dated Jun. 9, 2023.
Cen et al.: Chapter 2—A Real-Time Speech Emotion Recognition System and its Application in Online Learning. In Emotions and Technology, Academic Press, pp. 27-46. ISBN 9780128018569 (2016).
Co-pending U.S. Appl. No. 18/128,197, inventors Coelho Alves; José Carlos et al., filed Mar. 29, 2023.
Greeley et al.: Detecting Fatigue From Voice Using Speech Recognition. International Symposium on Signal Processing and Information Technology. pp. 567-571. doi:10.1109/ISSPIT.2006.270865 (2006).

(Continued)

*Primary Examiner* — Andrew W Johns
(74) *Attorney, Agent, or Firm* — SCHWEGMAN LUNDBERG & WOESSNER, P.A.

(57) ABSTRACT

A method for assessing whether one or more trackers are positioned on a person according to a predetermined configuration of tracker positions, comprising: transmitting, from a computing device to at least one tracker of the one or more trackers, an instruction to change an operation of the light emitter of the tracker to which the instruction is transmitted; taking one or more images by the optical sensing device; digitally processing the one or more images to digitally determine both first positions of a plurality of joints of the person on each image, and second positions of the one or more trackers positioned on the person on each image based on both a light of the light emitter of each of the one or more trackers and the transmitted instructions; digitally determining on which body member each of the one or more trackers is positioned on the person based on the first and second positions; and digitally comparing the position of each of the one or more trackers on the body members with the predetermined configuration of tracker positions.

20 Claims, 3 Drawing Sheets

(56) References Cited

OTHER PUBLICATIONS

Greeley et al.: Fatigue estimation using voice analysis. Behavior research methods. 39(3):610-619 doi:10.3758/BF03193033 (2007).
Jat et al.: Chapter 6—Voice Activity Detection-Based Home Automation System for People With Special Needs. Intelligent Speech Signal Processing, Academic Press (ISBN 9780128181300), pp. 101-111. doi:10.1016/B978-0-12-818130-0.00006-4 (2019).
Kuldip et al.: Chapter 6—Robust Speech Recognition Under Noisy Ambient Conditions. Human-Centric Interfaces for Ambient Intelligence, Academic Press (ISBN 9780123747082), pp. 135-162. doi:10.1016/B978-0-12-374708-2.00006-1 (2010).
PCT/EP2022/052707 International Search Report and Written Opinion dated May 18, 2022.
PCT/EP2022/057901 International Search Report and Written Opinion dated Jul. 18, 2022.
European Application Serial No. 22717630.2, Invitation pursuant to Article 94(3) and Rule 71(1) EPC dated Oct. 6, 2023, 5 pgs.
International Application Serial No. PCT/EP2022/057901, International Preliminary Report on Patentability dated Oct. 12, 2023, 9 pgs.

* cited by examiner

DIGITAL ASSESSMENT OF POSITION OF MOTION TRACKERS ON A PERSON

CROSS-REFERENCE TO RELATED APPLICATIONS

This application is a continuation of International Application No. PCT/EP2022/057901, filed internationally on Mar. 25, 2022, which claims priority to European Application No. 21398004.8, filed on Mar. 30, 2021, all of which are hereby incorporated by reference in their entireties.

TECHNICAL FIELD

The present disclosure relates to the technical field of motion tracking systems. More particularly, it relates to digital assessment of the placement of motion trackers on a person so that accurate motion tracking sequence of the person or body members thereof can be provided.

STATE OF THE ART

Many motion tracking systems have motion trackers, also referred to herein as trackers or inertial measurement units (IMUs), that are arranged on the target whose motion is to be tracked. The trackers include inertial sensors that measure e.g. orientations, angular velocities, accelerations, forces, etc., which may then be used to derive the motion of the tracked target.

One of the problems of motion tracking systems relying on motion trackers is that the motion tracking sequence provided is influenced by the positioning of the trackers. The computing device in charge of providing the motion tracking sequence considers that each particular tracker is arranged on a certain position on the tracked target, and the measurements from the respective inertial sensors represent how said certain position has moved over time. Non-correspondence between the position considered by the computing device and the actual position of the tracker results in the provision of a motion tracking sequence that is not accurate.

Inaccurate motion tracking sequences are particularly problematic when the person conducts a physical rehabilitation procedure using a motion tracking system. The person does not require the supervision of a doctor or therapist thanks to the motion tracking system, which digitally and automatically supervises the rehabilitation procedure. In rehabilitation procedures, the person has to exercise by moving body members in a certain way to recover the mobility of an injured part of the body or reduce the pain that the person suffers, for example by performing stretching movements. With these procedures, the user can recover from a hip injury, a shoulder injury, a neck injury, etc. more rapidly. When the movements are incorrectly supervised, the person that rehabilitates runs the risk of getting injured even if she/he knows which movements she/he must perform because the person does not know whether all the movements and repetitions thereof are correctly reproduced.

In order to provide an accurate motion tracking sequence so that the motion of the target can be correctly supervised by the motion tracking system itself, the trackers need to be correctly positioned on the person, i.e. the actual positions of the trackers have to coincide or fulfill the positions that the computing device expects the trackers to be on. Accordingly, there is a need for digitally assessing whether the trackers are correctly positioned on the person.

SUMMARY

A first aspect of the disclosure relates to a method for assessing whether one or more trackers are positioned on a person according to a predetermined configuration of tracker positions, a motion tracking system comprising the one or more trackers, an optical sensing device, and a computing device, each of the one or more trackers being adapted to be arranged on a body of the person and comprising a light emitter, a first antenna and at least one inertial sensor, the computing device comprising a second antenna, the method comprising:

transmitting, from the computing device to at least one tracker of the one or more trackers, an instruction to change an operation of the light emitter of the tracker to which the instruction is transmitted;

taking one or more images by the optical sensing device after the transmission of the respective instruction to the at least one tracker, the one or more images at least including a portion of the person where the one or more trackers are positioned;

digitally processing, by the computing device, the one or more images to digitally determine both first positions of a plurality of joints of the person on at least one image (or some images, or each image) of the one or more images, and second positions of the one or more trackers positioned on the person on at least one image (or some images, or each image) of the one or more images, the computing device determines the second positions based on both a light of the light emitter of each of the one or more trackers and the transmitted instructions;

digitally determining, by the computing device, on which body member each of the one or more trackers is positioned on the person based on the first and second positions; and digitally comparing, by the computing device, the position of each of the one or more trackers on the body members with the predetermined configuration of tracker positions.

The computing device assesses the location of the motion trackers on the body members of the person by way of the light they provide following the instructions of the computing device and the image(s) taken.

The computing device communicates with the one or more trackers wirelessly by means of the antennas. Owing to the wireless communications, the computing device establishes the number of trackers in the motion tracking system and some identity value or values of said tracker(s). For example, the computing device receives from the tracker (s) the MAC (medium access control) address and/or an IP (internet protocol) address as identity value(s). The identity value(s) may vary depending on the type of communications used (e.g. Bluetooth, Zigbee, WLAN, UMTS, LTE, etc.) or the identity data present in the trackers. The computing device transmits, to one or more particular trackers, instructions to change the operation of the light emitter thereof so that the one or more images taken afterwards can be used to detect and locate one, some or all the trackers of the one or more trackers. The one or more trackers may comprise a plurality of trackers.

A person or the computing device can trigger the taking of images by the optical sensing device. The computing device is communicatively coupled with the optical sensing device so that the image or images taken can be received for their digital processing by at least one processor of the device. The digital processing involves computer vision techniques known in the art for the detection and identification of significant elements. Each position corresponds to a pixel or, more typically, a group of pixels in the image; when it corresponds to a group of pixels, the position is preferably a center of the group (e.g. half of the width and half of the height of a rectangle encompassing the group of pixels with each side of the rectangle being tangent to the group of pixels, that is to say, with no rows or columns in which there are no pixels of the group of pixels; round, floor or ceiling functions can be applied to the halves in case they are not natural numbers). In this way, the first and second positions are determined by the computing device. The first and second positions can be determined as 2D coordinates or 3D coordinates; regarding the latter, some existing computer vision techniques are capable of processing the different colors present in images and shades thereof to infer depth and, hence, compute the depth dimension.

For the first positions, which are of the joints of the person, the computing device attempts to find as many joints as possible in the one or more images so as to have a set of first positions that represents part of the body of the person; with the set of first positions, the computing device derives which joint each first position is e.g. based on the location thereof, the existence of the other first positions and distances thereto. This can be attained by means of digital libraries and algorithms known in the art for joint identification and pose estimation from images, for instance but without limitation, Google's TensorFlow Pose estimation, Google's MediaPipe Pose and BlazePose, the algorithm described in "Reconstructing 3D Human Pose from 2D Image Landmarks" by V. Ramakrishna, etc.

The computing device uses the correspondence between emission of light (and, optionally, a color of the emitted light), the instruction transmitted to the tracker(s), and the moment the image or images were taken in accordance with the instruction(s) transmitted. For the detection of the trackers several strategies can be used.

By way of one example, only one light emitter is to be active each time, thus the computing device transmits instructions to one tracker to turn its light emitter on and to another tracker or trackers to turn their light emitters off.

By way of another example, the light emitters are to be sequentially active, in which case the computing device commands a first tracker to turn its light emitter on while the other light emitters are turned off (or are commanded to be turned off by the computing device) and the device detects and locates said tracker; then, without turning that light emitter off, the computing device commands the turning of another light emitter on so that the tracker can be detected and located, then another light emitter and so on.

By way of yet another example, the instructions transmitted by the computing device change the operation of the light emitter to turn off or on and also change the light of the light emitter to a given color; by commanding a different color to each tracker, the computing device may detect and locate all trackers while all the light emitters are turned on, thereby requiring fewer images and reducing the time it takes to locate all trackers.

Other strategies involving the turning of the light emitters on and off, and changing the light colors thereof are also possible for the assessment of the position of the trackers; in this sense, the computing device may as well not have to turn off light emitters of trackers that have been already detected and located for detecting and locating other trackers whose positions are yet to be assessed, namely, the computing device can take into account previous tracker detections and locations when detecting and locating other trackers with light emitters turned on. The computing device uses the identity value(s) of each tracker to transmit the instructions to the intended trackers so that one or a plurality of trackers can be detected and located based on the instructions.

The computing device analyzes the second positions taking into account the first positions to establish on which body member each second position (and, thus, each tracker) is. After determining the position of each tracker on the body, the computing device compares the positions with the predetermined configuration of tracker positions (e.g. stored in a memory of the computing device or a server communicatively coupled with the computing device so that the latter can retrieve it from said server).

The predetermined configuration of tracker positions comprises data indicative of where each tracker should be located on the person for the motion tracking activity that is to be performed by the person that uses the motion tracking system. For example, when the activity is physical exercising or rehabilitation, the exercises or routine to be performed by the person have a configuration of trackers on the person associated therewith so that the motion tracking sequence of the relevant body members (or of the entire person) can be provided and, thus, be digitally assessed by the computing device. By way of example, if the exercise or routine of exercises involves movements of a leg, the predetermined configuration of tracker positions may be one tracker on the hip, one tracker on the thigh, and one tracker on the shank, hence the computing device assesses the determined positions of the trackers by comparing the determined positions with the listed positions in the predetermined configuration. In this manner, it can be digitally verified whether the person has correctly positioned the one or more trackers on its body for the motion tracking activity.

In the context of the present disclosure, correct and incorrect positioning of trackers respectively refer to positioning of trackers coinciding or fulfilling the predetermined configuration of tracker positions, and not coinciding or not fulfilling the predetermined configuration of tracker positions.

In some embodiments, the method further comprises taking at least one image by the optical sensing device either before the first transmission of instructions to the one or more trackers, or after the transmission of the respective instruction to the at least one tracker such that no tracker is commanded to have its light emitter turned on, the at least one image at least including a portion of the person where the one or more trackers are positioned.

The computing device may more easily locate the lights of the light emitters comparing an image (or images) in which one or more light emitters are turned on with an image (or images) in which no light emitter is turned on. The processing of the at least one image with no light emitters turned on allows to establish the different colors on the images, the person, the background, etc. so that lights can be recognized more easily by computer vision techniques in other image or images.

In some embodiments, the one or more images are taken while the person is standing upright. In some embodiments, the one or more images are taken while the person is standing still.

The assessment of the positions of the trackers becomes computationally simpler and the assessment made is more accurate when the person with the trackers thereon is standing in an upright position and/or the person does not move.

Notwithstanding, as long as the one or more images at least include the portion of the person where the one or more trackers are positioned, other postures are also possible, and the person might also move while the image(s) is taken.

In some embodiments, the method further comprises commanding or transmitting an instruction to the optical sensing device, by the computing device, to take the one or more images after the transmission of the respective instruction to change an operation of the light emitter to the at least one tracker.

The computing device can automatically command the image taking following the transmission of instructions to change the operation of one or more light emitters, thereby simplifying the process.

In some embodiments, the optical sensing device at least comprises first and second cameras. In some of these embodiments, the one or more images taken by the optical sensing device and digitally processed by the computing device comprise two or more images with at least one image taken with the first camera and at least one image taken with the second camera.

In some embodiments, the motion tracking system or the optical sensing device comprises a depth sensor. In some of these embodiments, the one or more images taken by the optical sensing device and digitally processed by the computing device further comprise depth data.

The use of two or more cameras enables the use of stereoscopy to determine depth or tridimensional data of objects within the images. The computing device digitally processes the images to provide the first positions and/or the second positions as three-dimensional points in space, hence in these cases the use of the two cameras can provide or ease the provision (for computer vision techniques) of 3D coordinates, or provide such coordinates with superior accuracy than when the computer vision techniques process images from the optical sensing device with e.g. one camera.

The depth sensor likewise provides or eases the provision of 3D coordinates about the first and/or second positions, or provide such coordinates with superior accuracy. Depth sensors typically use laser and measure time of flight of emitted signals for establishing the three dimensions of objects.

In some embodiments, the computing device comprises the optical sensing device.

In some embodiments, the method further comprises: commanding, by the computing device, provision of one or more user perceptible signals relative to a result of the digital comparison.

The person that is using the trackers or a person within the premises can get to know the assessment made by the computing device about the position of the one or more trackers by way of user perceptible signals. To this end, the motion tracking system comprises one or more devices adapted to provide user perceptible signals, for example, one or more of: a screen, loudspeakers, vibrating devices, light emitters, etc. Any one of the devices for provision of user perceptible signals may be embedded in the trackers or the computing device, or be separate devices.

In some embodiments, the result of the digital comparison is indicative of at least one tracker being incorrectly positioned.

One or more trackers are considered as erroneously positioned according to the predetermined configuration of tracker positions. This means that the determined positions do not match with those indicated in the predetermined configuration of tracker positions or, in some cases, the determined positions are too far away from the intended positions or areas as indicated in the predetermined configuration of tracker positions. To this end, one or more thresholds or ranges can be registered in the predetermined configuration of tracker positions to define maximum acceptable variation in position of the trackers relative to the intended positions or areas.

Further, the erroneous positioning of one or more trackers might not only be because the determined position of a tracker does not match with one of the positions indicated in the predetermined configuration of tracker positions, but also because the predetermined configuration of tracker positions indicates that a tracker shall be positioned on a certain body member (and/or with a certain position) yet the computing device has not located any tracker that matches such position.

For example, the predetermined configuration of tracker positions indicates that there shall be a first tracker on a left upper arm, a second tracker on a left lower arm, and a third tracker on a chest, and the computing device has only located two trackers, one on the left upper arm and one on the left lower arm. In this example, the computing device determines that at least one tracker is incorrectly positioned as well.

In some embodiments, the one or more user perceptible signals are indicative of at least one of: incorrect positioning of at least one tracker, and guidance on how to reposition at least one incorrectly positioned tracker.

In some embodiments, the method further comprises repeating the steps of transmitting, taking one or more images, digitally processing the one or more images, digitally determining on which body member each of the one or more trackers is positioned and digitally comparing after the provision of the one or more user perceptible signals in order to assess whether the person has repositioned the one or more trackers according to the predetermined configuration of tracker positions.

Following the provision of user perceptible signals indicating that one or more trackers are erroneously placed, the person can reposition trackers on her/his body based on the information provided in the user perceptible signals. Since the person may once again erroneously position one, some or all trackers, instructions to change the operation of the light emitters are transmitted once again (to one, some or all trackers), one or more images are taken again, and the computing device assesses the position of trackers (of one, some or all of them) to determine whether the repositioning by the person resulted in a correct placement. It is noted that the computing device may be configured to assume that the trackers that were previously correctly positioned will remain correctly positioned after the repositioning by the person, in which case the computing device does not assess the positions of these trackers anew. Alternatively, the computing device may be configured to not assume that correctly-positioned trackers will remain correctly positioned after the repositioning by the person and, hence, assess the positions of these trackers anew. A person may inadvertently move trackers while repositioning others, so for a greater confidence level in the motion tracking procedure the position of all trackers may be assessed once again.

In some embodiments, the computing device conducts the steps of transmitting and taking one or more images a plurality of times; the computing device conducts each step of taking one or more images after having transmitted instructions to the one or more trackers so that only the light emitter of one tracker emits light, i.e. the light emitter of remaining trackers does not emit light.

In some embodiments, the step of transmitting comprises transmitting instructions to each of the one or more trackers to change the operation of the light emitter thereof so that it emits light with a color different from a color of the light of the other light emitters; and the computing device determines the second positions based on both the color of the light of the light emitter of each of the one or more trackers and the transmitted instructions.

In some embodiments, the step of digitally determining the body member on which each tracker is positioned comprises: digitally computing distances between each second position and all first positions thereby providing a set of distances per second position; and determining that each tracker is positioned on the body member that extends between respective first and second joints, the first and second joints being the joints corresponding to the two first positions having a shortest distance to the second position corresponding to the tracker.

The set of distances per second positions reveals which are the joints (among all the detected joints) that are closest to the second positions, that is to say, that are closest to each tracker. The computing device determines that the trackers are on the body members that extend between the two joints (resulting in a segment defining the body member) with shortest distances to the tracker, e.g. if the joints are the hip and a knee, the body member is a thigh or upper leg.

The distances can be Euclidean distances, for example. When the first and second positions are 2D points, the distances are computed in two dimensions, whereas when the first and second positions are 3D points, the distances are computed in three dimensions.

In some embodiments, the step of digitally determining the body member on which each tracker is positioned comprises: digitally computing distances between each second position and all first positions thereby providing a set of distances per second position; digitally providing, for each tracker, a set of candidate body members on which the tracker can be positioned, each candidate body member having a first joint that is the joint corresponding to the first position having a shortest distance to the second position corresponding to the tracker; and digitally selecting, for each tracker, a body member of the set of candidate body members, the selected body member having a second joint corresponding to the first position that has a shortest distance in the set of distances (that is to say, the first position of its second joint has a distance to the second position corresponding to the tracker that is the shortest).

The provision of a set of candidate body members increases the confidence in the determination of the position of the one or more trackers on respective body members, especially when the tracker or trackers are not correctly positioned on the body member.

In some embodiments, the step of digitally determining the body member on which each tracker is positioned comprises: digitally computing distances between each second position and all first positions thereby providing a set of distances per second position; and determining that each tracker is positioned on a body member by using triangulation with three distances of the set of distances. In some of these embodiments, the three distances correspond to the three first positions having a shortest distance to the second position corresponding to the tracker.

The position of the tracker on a particular body member can be inferred from the intersection of the three distances following a triangulation procedure. The distance of the tracker to each of the three joints is indicative of the body member on which the tracker is placed.

With regards to the aforesaid embodiments, it is to be noted that the location of a second position relative to one or more first positions can also be used in some embodiments to determine on which body member a tracker is. By way of an example, if on one or more images a second position is beneath a first position corresponding to a hip joint, the computing device may determine that the tracker is on an upper leg. By way of another example, if on one or more images a second position is on the left relative to a first position corresponding to a (person's) left elbow joint, the computing device may determine that the tracker is on the chest.

In some embodiments, the step of digitally determining the body member on which each tracker is positioned comprises: digitally establishing an angular relationship between each second position and one, some or all first positions thereby providing a set of angular relationships per second position; and determining that each tracker is positioned on the body member whose segment extending between respective first and second joints matches one, some or all angular relationships of the respective set of angular relationships, the first and second joints being joints corresponding to two first positions.

The location of second positions relative to one or more first positions defines an angular relationship (e.g. a second position beneath a first position defines an angular relationship of −90°). With one or more angular relationships, the body member where a second position is can be determined. When multiple angular relationships are used, the computing device might use triangulation with said relationships to determine the body member. Additionally, in some embodiments the computing device computes distances in the manner described before, and the determination of the body member where a tracker is on is established based on both the angular relationship(s) and one or more distances.

For the determination of the position of the one or more trackers in this manner, the person is preferably standing upright when the one or more images are taken. The angular relationships can be defined when the first and second positions are defined as 2D coordinates, and even when they are defined as 3D coordinates but with the depth coordinate ignored (namely, the first and second points are projected onto a coronal plane).

In some embodiments, the step of digitally determining the body member on which each tracker is positioned further comprises digitally determining a tracker position on the body member for each tracker, the tracker position comprising a position of the tracker along a length direction of the respective body member on which the tracker is positioned.

The computing device additionally computes positions of trackers along the length of the body members, i.e. positions along the segments. Such length positions are indicative of where along the entire length of the body member each tracker is positioned.

In some embodiments, the step of digitally comparing further comprises, at least for the trackers of the one or more trackers that are positioned on the correct body members according to the predetermined configuration of tracker positions:
  digitally computing:
    distances of the trackers to the two first positions corresponding to the two joints to which the body member is connected, said distances being along the length direction (i.e. between the first positions of the joints of the respective body member on which the tracker is positioned and the length position of the respective tracker position); or
    distances of the trackers to one of the first positions corresponding to the one of the joints to which the body member is connected and a length of the body member, said distances being along the length direction; and
  digitally comparing the distances of the trackers to the first positions corresponds to the joints with respective predetermined distance ranges in the predetermined configuration of tracker positions.

The computing device also determines whether the position of the trackers along the length of the respective body member is correct according to the predetermined configuration of tracker positions. In this sense, the device computes the distances between the position of the tracker and each pair of joints, or the distance between the position of the tracker and one of the joints together with the length of the body member (the length of the body member is the distance between the two respective joints).

With the first option, ratio or percent values can be computed indicating how far the tracker is along the length of the body member with respect to each of the two joints, so it is not necessary to compute the length of the body member. With the second option, the ratio or percent values can also be computed.

The ratios or percent values are compared by the computing device with predetermined threshold or range values set in the predetermined configuration of tracker positions so that it can be determined if the positioning of the tracker along the length of the body member is correct. By way of example, for the tracker to be correctly positioned on a particular body member, its length position shall be within a respective predetermined range, e.g. between 35% and 65% of the length of the segment.

In some embodiments, the tracker position further comprises a position along a direction perpendicular to the length direction of the respective body member on which the tracker is positioned.

The direction perpendicular to the length direction can also be referred to as width direction, and this position be referred to as width position. Said position defines whether the tracker is positioned on the internal or external part of the body member, and how far from the segment defined by the respective two joints.

The width position may also influence the measurements made by the inertial sensors; hence, the assessment of this position can also improve the motion tracking.

In some embodiments, the step of digitally comparing further comprises, at least for the trackers of the one or more trackers that are positioned on the correct body members according to the predetermined configuration of tracker positions: digitally computing angles formed by both first vectors and second vectors, each first vector extending from a body member segment to the position of the respective tracker along the direction perpendicular to the length direction, and each second vector being one of: an orientation of a body member on which the respective tracker is positioned, an orientation of a joint of said body member, and an orientation of a predetermined body member; and digitally comparing the angles of the trackers with respective predetermined angular ranges in the predetermined configuration of tracker positions.

The computation of the angles is based on two directions: a first direction that goes from the segment of the concerned body member and the width position of the tracker, and a second direction that relates to the orientation of either the body member or the joint that it is connected thereto, or the orientation of a predetermined body member that is expected to have an orientation that is similar to the one of the body member on which the tracker is positioned.

Preferably, the computing device uses the orientation of the body member on which the tracker is positioned or the orientation of one of the two joints, but when it is not possible to establish any one of such orientations accurately (by way of computer vision techniques with which the one or more images are processed, or by way of orientation measurements provided by the tracker positioned on the body member), then the orientation of a predetermined body member is used instead.

The orientation of the body member represents the direction along which a predetermined edge of the body member is facing; the predetermined edge is typically selected to be a front-most edge, thus if the body member is rotated towards one side, the orientation represents such rotation.

The orientation of the joint, which is considered to be the same or substantially the same as the orientation of the body member, represents the direction along which predetermined edge of the joint is facing; the predetermined edge is typically selected to be a front-most edge. In addition to computer vision techniques, the orientation of the joint can be computed as a cross-product of the directions along which the body members that the joint is connected to extend. For instance, the orientation of the knee joint can be obtained by computing the cross-product of a first vector defined by the hip joint and the knee joint, and a second vector defined by the knee joint and the ankle joint.

A predetermined body member is preferably set in the computing device for each body member where a tracker can be arranged. For instance, the right foot or the chest can be the predetermined body member for the right thigh and right shank. The orientation of said predetermined body member is obtained by way of computer vision techniques with which the one or more images are processed; or, alternatively, by way of orientation measurements provided by the tracker positioned on the predetermined body member by way of orientation measurements provided by the tracker positioned on the predetermined body member (in those embodiments in which there is a tracker positioned thereon).

The angles are compared by the computing device with predetermined threshold or range values set in the predetermined configuration of tracker positions so that it can be determined if the positioning of the tracker along the width of the body member is correct. By way of example, for the tracker to be correctly positioned on a particular body member, the angle shall be within a particular angular region around the body member, something that can be assessed by way of a respective predetermined range, e.g. between −15° and 15° of a forward-facing direction of the body member.

In some embodiments, for digitally computing the angles the computing device: digitally defines a plane with a normal vector corresponding to a direction of a body member segment extending between the first positions corresponding to the two joints of the respective body member on which the tracker is positioned, the plane containing the second position corresponding to the tracker; and digitally computes the angle between the first vector (also referred to hereinafter as tracker vector) and a projection vector, the first vector being contained in the plane and extending between the body member segment and the second position corresponding to the tracker, and the projection vector being a projection of the second vector onto the plane.

In some embodiments, the predetermined configuration of tracker positions comprises data indicative of trackers positions on a particular body member having left and right same body members; and the step of digitally determining on which body member each of the one or more trackers is positioned on the person comprises, at least for the trackers of the one or more trackers that are positioned on a body member having left and right same body members, digitally determining on which of the left and right body member each of the one or more trackers is positioned.

The assessment of the positions of the tracker might also include determining on which of two same body members each tracker is.

By way of example, when one of the two arms shall have one or more trackers thereon, the predetermined configuration of tracker positions might indicate that for the motion tracking procedure to be performed it is the right arm the one that shall have the tracker(s) thereon. The person might incorrectly arrange the tracker(s) on the left arm, in which case the motion tracking procedure can be erroneous and may even result in the injury of the person if performing a physical rehabilitation procedure. The computing device determines that the one or more trackers are not on the right arm, so the computing device may halt or not start a motion tracking procedure until the one or more trackers are positioned according to the predetermined configuration of tracker positions and/or the computing device may inform the person that the one or more trackers are incorrectly positioned.

In some embodiments, the method further comprises digitally providing, by the computing device, a motion tracking sequence of one or more body members of the person based on measurements received from the one or more trackers when a result of the digital comparison is indicative of each of the one or more trackers being correctly positioned.

In some embodiments, the method further comprises digitally blocking, by the computing device, a motion tracking procedure thereby the computing device not providing a motion sequence when a result of the digital comparison is indicative of at least one tracker being erroneously positioned.

The knowledge of the positions of the trackers can be used by the computing device to allow or forbid the motion tracking procedure; accordingly, the computing device provides the motion tracking sequence when all the trackers are correctly positioned.

A second aspect of the disclosure relates to a motion tracking system comprising: one or more trackers adapted to be arranged on a body of a person, and comprising: a light emitter, a first antenna and at least one inertial sensor; an optical sensing device, and a computing device comprising a second antenna, the computing device being adapted to execute steps of the method according to the first aspect of the disclosure and/or embodiments thereof.

The motion tracking system is capable of digitally assessing how a person that is the user of the motion tracking system positions the one or more trackers thereon, being possible to determine whether the positioning of the tracker(s) fulfills a predetermined configuration of tracker positions.

In some embodiments, the optical sensing device at least comprises first and second cameras.

In some embodiments, the motion tracking system or the optical sensing device comprises a depth sensor.

In some embodiments, the computing device comprises the optical sensing device.

In some embodiments, the motion tracking system and/or the computing device comprises one or more devices adapted to provide user perceptible signals, for example, one or more of: a screen, loudspeakers, vibrating devices, light emitters, etc.

A third aspect of the disclosure relates to a data processing apparatus comprising at least one processor adapted to perform a method according to the first aspect of the disclosure and/or embodiments thereof.

A fourth aspect of the disclosure relates to a computer program product that has instructions which, when executed by a computing device, cause the computing device to perform a method according to the first aspect of the disclosure and/or embodiments thereof.

Upon running the computer program product on one or more processors of the computing device, the computing device assesses the placement of the one or more trackers on the body of the person.

In some embodiments, the computer program product is embodied on a non-transitory computer-readable medium or a computer-readable data carrier has the computer program product stored thereon.

A fifth aspect of the disclosure relates to a data carrier signal carrying a computer program product according to the fourth aspect of the disclosure.

Similar advantages as those described for the first aspect of the disclosure are also applicable to the second, third, fourth, and fifth aspects of the disclosure.

BRIEF DESCRIPTION OF THE DRAWINGS

To complete the description and in order to provide for a better understanding of the disclosure, a set of drawings is provided. Said drawings form an integral part of the description and illustrate embodiments of the disclosure, which should not be interpreted as restricting the scope of the disclosure, but just as examples of how the disclosure can be carried out. The drawings comprise the following figures.

DESCRIPTION OF EMBODIMENTS

Figure 1:
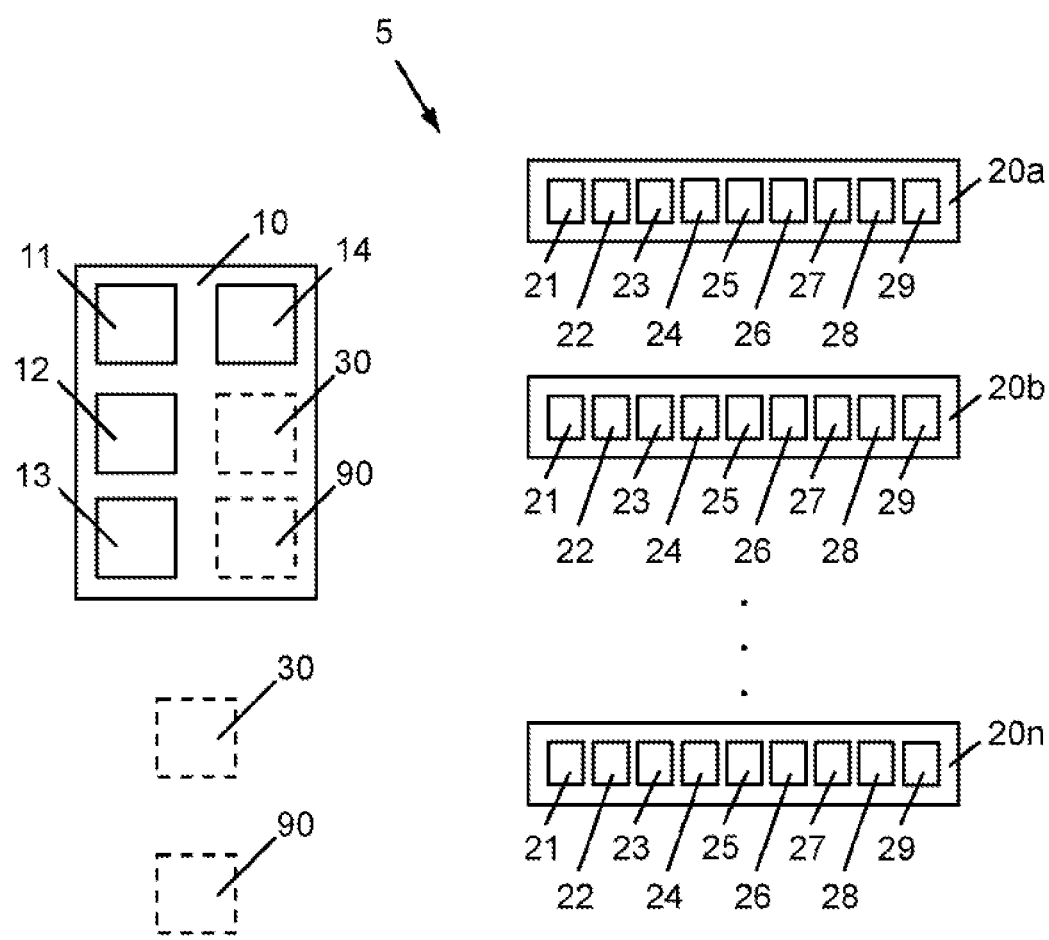
FIG. 1 diagrammatically shows a motion tracking system in accordance with embodiments.

FIG. 1 diagrammatically shows a motion tracking system 5 in accordance with embodiments. The motion tracking system 5 includes a computing device 10, which may be e.g. a tablet, a mobile phone, a personal computer, etc., an optical sensing device 30 (shown with dashed lines to illustrate that it can be part of the computing device 10 or be separate from the computing device 10), and one or more trackers 20$a$-20$n$, i.e. inertial measurement units.

Each tracker 20$a$-20$n$ includes one or more inertial sensors selected from e.g. an accelerometer 21, a gyroscope 22 and a magnetometer 23. In the embodiment of FIG. 1, each tracker 20$a$-20$n$ includes all three inertial sensors 21-23, but in other embodiments the trackers only include an accelerometer 21 and a gyroscope 22, for instance. Preferably, all IMUs 20$a$-20$n$ include the same inertial sensors 21-23.

The trackers 20$a$-20$n$ further include one or more light emitters 24 (e.g. one or more LEDs which can have adjustable light or not), at least one processor 25, at least one memory 26, and a first wireless communications module 27 for transmitting radiofrequency signals to and receiving radiofrequency signals from the computing device 10. For example, the trackers 20$a$-20$n$ transmit advertisement packages, data packets with identification data (e.g. one or more identities, keys, etc.), data packets with measurements of the inertial sensor(s) 21-23, etc., and receive packets from the computing device 10 with e.g. instructions to change operation of the one or more light emitters 24. When no wireless communications connections are established with the computing device 10, the radiofrequency signals of the trackers 20a-20n include advertisement packages for indicating their presence and that they are active. Once the wireless communications connections are established (using a technology and protocol known by a skilled person, for instance but without limitation, Bluetooth and Bluetooth Low Energy communications, cellular network communications such as GSM, UMTS or LTE, wireless LAN communications, etc.) with the computing device 10, the radiofrequency signals of the trackers 20a-20n may include identification data and/or the measurements, based on which the motion sequence will be provided by the computing device 10. A first antenna 28 for radiating and capturing electromagnetic waves is provided as part of the first wireless communications module 27.

Each tracker 20a-20n is adapted to be arranged on the body of a person so that the measurements provided by each tracker 20a-20n can be processed by the computing device 10, thereby providing a motion tracking sequence of the person. The trackers 20a-20n may be attached to body members of the person by means of an attaching device 29 like, for instance, straps, Velcro, etc., that the motion tracking system 5 or the tracker 20a-20n itself comprises.

Preferably, at least one processor 25 of the trackers 20a-20n runs a sensor fusion algorithm for processing the measurements of the inertial sensors 21-23 within the respective tracker. The sensor fusion algorithm is intended to enhance the raw measurements of the inertial sensors by correcting errors thereof due to drifts of the inertial sensors and, thus, outputs processed measurements that are to be transmitted to the computing device 10.

The computing device 10 includes at least one processor 11, at least one memory 12, and a second wireless communications module 13 for transmitting receiving radiofrequency signals to the trackers 20a-20n and receive radiofrequency signals therefrom. The second wireless communications module 13 includes at least a second antenna 14 whereby electromagnetic waves may be captured, and then processed by the at least one processor 11, and radiated as well.

Preferably, the motion tracking system 5 and/or the computing device 10 also includes at least one device 90 (shown with dashed lines to illustrate that it can be part of the computing device 10 or be separate from the computing device 10) for providing user perceptible signals like e.g. a screen or loudspeakers, to name a few examples. That is to say, the at least one device 90 comprises visual output means (e.g. screen, LEDs), audio output means (e.g. loudspeakers), vibrating means (e.g. a vibrator), etc. for providing user perceptible signals in the form of sounds, vibration, animated graphics, etc. When the at least one device 90 comprises a screen, the computing device 10 is capable of showing instructions and/or information to the intended user about the operation of the motion tracking system 5 and the motion tracking procedure to be conducted with the system 5, for example predetermined movements that are to be performed by an intended user of the motion tracking system 5, a predetermined configuration of tracker positions, including but not limited to indications of a correspondence between trackers 20a-n and body members of the person for positioning them thereon, results of the assessment of the positions of the trackers, etc. To this end, the computing device 10 stores, in the at least one memory 12, the predetermined configuration of tracker positions, and also data relative to the physical exercises, i.e. predetermined movements, of intended users. Any of these data can be transmitted to and/or received from another electronic device thanks to the second wireless communications module 13. For example, a therapist is able to receive the feedback at a computing device in a hospital so as to monitor the evolution of the person. Based on the feedback received, the therapist is able to adjust the difficulty of the movement(s), the number of repetitions thereof, prescribe new movements, etc. so that the person may further exercise using the motion tracking system 5.

The optical sensing device 30 is adapted to take images and can be, for example, a digital camera, a mirrorless camera, etc. And as aforesaid, the optical sensing device 30 is, in some embodiments, comprised in the computing device 10.

In some embodiments, the optical sensing device 30 comprises two or more cameras, in which case stereoscopy could be used to determine a depth dimension of what is captured in the images.

In some embodiments, the optical sensing device 30 or the motion tracking system 5 comprises a depth sensor for determining a depth dimension.

Figure 2A:
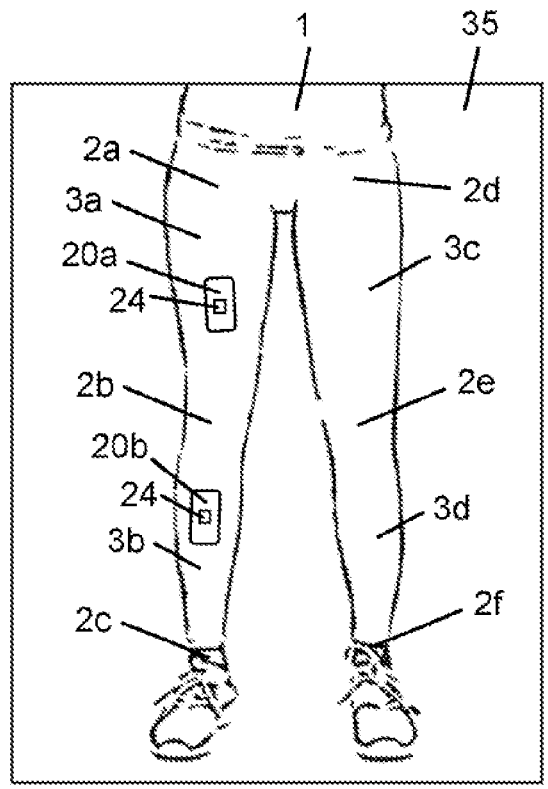
FIG. 2A shows an image of a person with trackers positioned on her body in accordance with embodiments, and FIG. 2B diagrammatically shows first and second positions computed by a computing device.

FIG. 2A shows an image 35 of a person 1 taken with an optical sensing device. The image 35 includes a portion of the person 1 with the two trackers 20a, 20b of the motion tracking system positioned thereon. In some embodiments, the image 35 includes the entire person 1.

A first tracker 20a is positioned on a (person's) right thigh 3a (connected to right hip 2a and right knee 2b joints), and a second tracker 20b is positioned on a (person's) right shank 3b (connected to right knee 2b and right ankle 2c joints). The first and second trackers 20a, 20b have their respective light emitters 24 facing towards the optical sensing device.

Figure 2B:
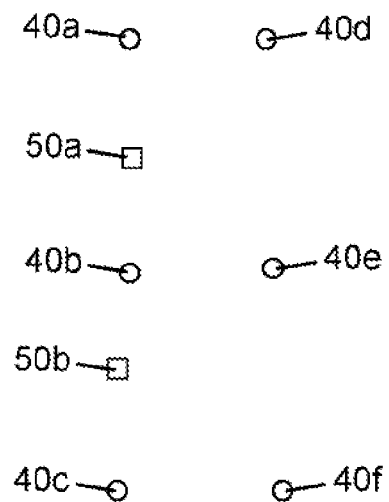
Figure 3:
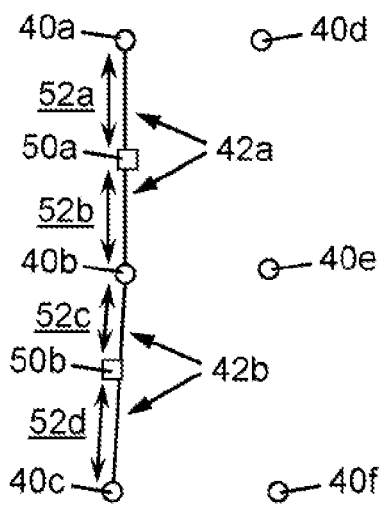
FIGS. 3-4 diagrammatically show the determination of tracker positions in accordance with embodiments.
Figure 4:
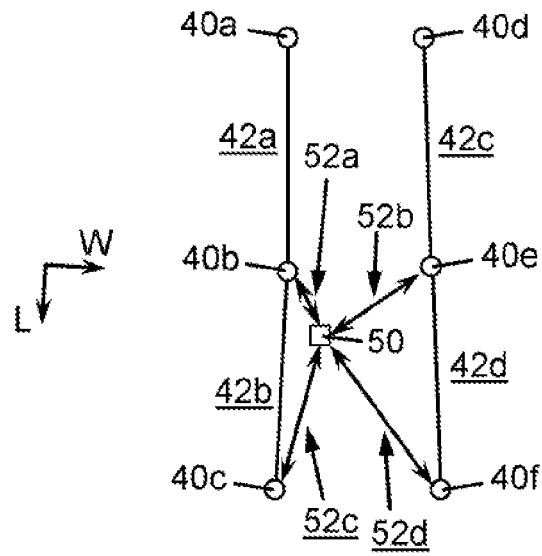

A computing device of a motion tracking system in accordance with embodiments processes the image 35 with computer vision techniques so as to detect and identify a set of first positions 40a-40f, shown in FIGS. 2B, 3 and 4 with circles for illustrative purposes only. The processing makes possible to provide coordinates for each of the first positions 40a-40f, each of which corresponds to a joint 2a-2f of the person 1. The coordinates can be two-dimensional like (x, y), or even three-dimensional like (x, y, z). A different representation of the coordinates is possible without departing from the scope of the present disclosure. Additionally, based on the portion of the person 1 captured in the image 35 and/or the distribution of first positions 40a-40f, the computer vision technique is capable of labeling each first position 40a-40f with a joint name. For example, it can label the first position 40a on the top-left part with a name or encoded value standing for 'right hip', label the first position 40b beneath the previous first position 40a with a name or encoded value standing for 'right knee', etc.

Likewise, the computing device commands the light emitters 24 of the different trackers 20a, 20b to turn on or off, or change the light thereof, so that based on the light emission it is capable of establishing in the image 35 (or images) which tracker 20a, 20b is which. Accordingly, depending on the number of trackers 20a, 20b on the person 1 and the strategy followed by the computing device to have light emitted by the trackers 20a, 20b, more or fewer images 35 might be necessary to provide a set of second positions 50a, 50b, shown in FIGS. 2B, 3 and 4 with squares for illustrative purposes only.

FIG. 2B diagrammatically shows first positions 40a-40f, corresponding to joints 2a-2f, and second positions 50a, 50b, corresponding to trackers 20a, 20b, as computed by the computing device. With the determination of the first and second positions 40a-40f, 50a, 50b, the computing device may derive on which body member each of the first and second tracker 50a, 50b is based on the distribution of second positions 50a, 50b among the first positions 40a-40f.

The computing device may derive that the first tracker 20a is on the right thigh 3a because the second position 50a of the first tracker 20a is between two first positions 40a, 40b corresponding to the right hip 2a and right knee 2b; and that the second tracker 20b is on the right shank 3b because the second position 50b of the second tracker 20b is between two first positions 40b, 40c corresponding to the right knee 2b and right ankle 2c. Distances between each second position 50a, 50b and some or all first positions 40a-40f might be computed to derive that the trackers 20a, 20b are positioned in that manner.

After deriving this positioning, the computing device can assess whether the positions are correct according to a predetermined configuration of tracker positions. Exemplary predetermined configurations can be like the ones shown in Tables 1 to 3.

TABLE 1

Exemplary predetermined configuration of tracker positions for a first exercise.

| Exercise 1 | Position |
| --- | --- |
| Tracker 1 | Right thigh |
| Tracker 2 | Right shank |

TABLE 2

Exemplary predetermined configuration of tracker positions for a second exercise.

| Exercise 2 | Position |
| --- | --- |
| Tracker 1 | Right lower arm |
| Tracker 2 | Right upper arm |

TABLE 3

Exemplary predetermined configuration of tracker positions for a third exercise.

| Exercise 3 | Position |
| --- | --- |
| Tracker 1 | Right thigh |
| Tracker 2 | Right shank |
| Tracker 3 | Left thigh |
| Tracker 4 | Left shank |

With regards to the first example, the computing device compares the determined positions with those of the predetermined configuration of tracker positions and establishes that the trackers are correctly positioned.

Turning to the second and third examples, the computing device compares the determined positions with the ones in the predetermined configurations of tracker positions and establishes that the trackers are incorrectly positioned. In the second example, the trackers shall be positioned on the right upper and lower arm yet they are on the right upper and lower leg. In the third example, two trackers are correctly positioned but the computing device cannot find two additional trackers matching the positions of Tracker 3 and Tracker 4 as specified in the predetermined configurations of tracker positions.

FIG. 3 diagrammatically shows the determination of tracker positions, including length positions, in accordance with embodiments. In this example, the sets of first and second positions 40a-40f, 50a, 50b correspond to the example of FIGS. 2A-2B. A computing device of a motion tracking system in accordance with embodiments has already determined that the first tracker 20a is on the right thigh 2a and the second tracker 20b is on the right shank 2b. Corresponding body member segments 42a, 42b have been illustrated extending between respective first positions 40a-40c for the sake of clarity.

In order to compute a length position for the tracker positions, a first distance 52a is computed for the second position 50a of the first tracker 20a from said second position 50a and a first position 40a from which the body member segment 42a extends, and a second distance 52b is also computed in the same manner but from the other first position 40b from which the body member segment 42b extends. The same is done for the second position 50b of the second tracker 20b but for the first positions 40b, 40c of the respective body member segment 42b, thereby providing distances 52c, 52d.

The distances 52a-52d computed represent length positions of the trackers 20a, 20b, thus the position of the trackers 20a, 20b along the length of the body members 2a, 2b is also determinable by the computing device. The length positions may also be assessed by the computing device, for instance by comparing them with length positions if indicated in the predetermined configuration of tracker positions, like in the example of Table 4 below.

TABLE 4

Exemplary predetermined configuration of tracker positions for a fourth exercise.

| Exercise 4 | Position | Length Position from Upper Joint | Length Position from Lower Joint |
| --- | --- | --- | --- |
| Tracker 1 | Right shank | 30%-80% | 20%-70% |
| Tracker 2 | Right thigh | 35%-65% | 35%-65% |

The computing device first matches the tracker 1 of the predetermined configuration with the second tracker 20b, and the tracker 2 of the predetermined configuration with the first tracker 20a. Then, in order to determine that the positioning of the first and second trackers 20a, 20b is correct, the computing device shall verify the length positions of each tracker 20a, 20b. Although in this example the length positions of the predetermined configuration of tracker positions are referred to upper and lower joints, it will be noted that other joint definitions are also possible within the scope of the present disclosure.

Concerning tracker 2 (the first tracker 20a), a first distance 52a that is a length position from the right hip 2a joint shall be equal to or greater than 35% and equal to or less than 65% of the length of the body member (thigh) segment 42a, which is the distance computed between the respective two first positions 40a, 40b; further, a second distance 52b that is a length position from the right knee 2b joint shall be also between 35% and 65% of the length of the body member segment 42a.

Concerning tracker 1 (the second tracker 20b), a third distance 52c that is a length position from the right knee 2b joint shall be equal to or greater than 30% and equal to or less than 80% of the length of the body member (shank) segment 42b; further, a fourth distance 52d that is a length position from the right ankle 2c joint shall be equal to or greater than 20% and equal to or less than 70% of the length of the body member segment 42*b*.

In this case, the length positions of the two trackers 20*a*, 20*b* fulfills the length position ranges defined in the predetermined configuration of tracker positions, thus the computing device determines that the trackers 20*a*, 20*b* are correctly positioned.

FIG. 4 diagrammatically shows the determination of tracker positions in accordance with embodiments. In this example, the set of first positions 40*a*-40*f* corresponds to the example of FIGS. 2A-2B. Body member segments 42*a*-42*d* corresponding to both thighs and both shanks have been represented for illustrative purposes only. A computing device of a motion tracking system in accordance with embodiments has found a second position 50 close to the first position 40*b* of the right knee.

The computing device intends to establish on which body member the tracker corresponding to the second position 50 is, and it computes distances 52*a*-52*d* between the second position 50 and all first positions 40*a*-40*f* (for the sake of clarity only, the distances to the two top-most first positions 40*a*, 40*d* have not been represented).

With the computed distances 52*a*-52*d*, the computing device may proceed in the way described with reference to FIG. 3, or alternatively may proceed in one of the three following ways:

Find the first position 40*b* that is closest to the second position 50 by finding the minimum distance in the set of distances 52*a*-52*d*. With said first position 40*b*, the device provides a set of candidate body members which are connected to said joint. Since the first position 40*b* corresponds to the right knee joint, in this case the candidate body members are the right thigh and the right shank. Then, the device determines that the tracker is on the body member of the candidate body members whose other joint has the shortest distance to the tracker. In this case, the distance 42*b* to the first position 40*c* corresponding to the right ankle is shorter than the distance to the first position 40*a* of the right hip.

Determine on which body member the tracker is by triangulation with three distances 52*a*-52*d*, preferably the shorter ones 52*a*-52*c* for simpler deduction of the body member. In this regard, the computing device may have stored or retrieve from a server a set of distance ranges to different joints per body member, so for shanks the set of distance ranges indicate how short or long the distance to same-leg knee joint can be, how short or long the distance to same-leg ankle can be, how short or long the distance to other-leg knee joint can be, etc. So, when the concerned distance ranges are met, the computing device determines that the second position 50 is on the respective body member.

The distance ranges are preferably but not necessarily stored as percent ranges, thereby making possible to use same sets of distance ranges irrespective of the height of the person or the length of the body members of the person. In that case, the computing device first computes a height or length of the body members of the person by processing the one or more images, and adjusts the distance ranges according to the computed height or lengths.

Further, the triangulation process can also be used to determine length position and/or width position of the tracker, namely, where along the length axis (a length axis L for the body member segment 42*b* of the shank is shown for the sake of clarity) of the body member the tracker is and/or where perpendicularly to the length axis (a width axis W for the body member segment 42*b* of the shank is shown for the sake of clarity) of the body member the tracker is. It is to be noted that different L and W axes would be represented for other body member segments since they depend upon the direction in which the body member segment extends.

Compute the angular relationship that exist between the second position 50 and one or more first positions 40*a*-40*f*, i.e. compute the angle formed by the second position 50 and one or more first positions 40*a*-40*f* (with e.g. a polar grid). For example, the angular relationship between the second position 50 and the first position 40*b* corresponding to the right knee is 295° (using the first position 40*b* as the reference), and the angular relationship between the second position 50 and the first position 40*e* corresponding to the left knee is 215° (using the first position 40*e* as the reference). In this case, the computing device might determine on which body member the second position 50 is with just two angular relationships; in other examples, one angular relationship may suffice, or three or angular relationships may be needed. In embodiments in which the first positions 40*a*-40*f* and the second position 50 are provided as 3D coordinates, the positions are first projected onto the coronal plane so as to provide 2D angular relationships.

With each of these ways, the computing device determines that the second position 50 is on the body member segment 42*b* of the right shank.

Figure 5:
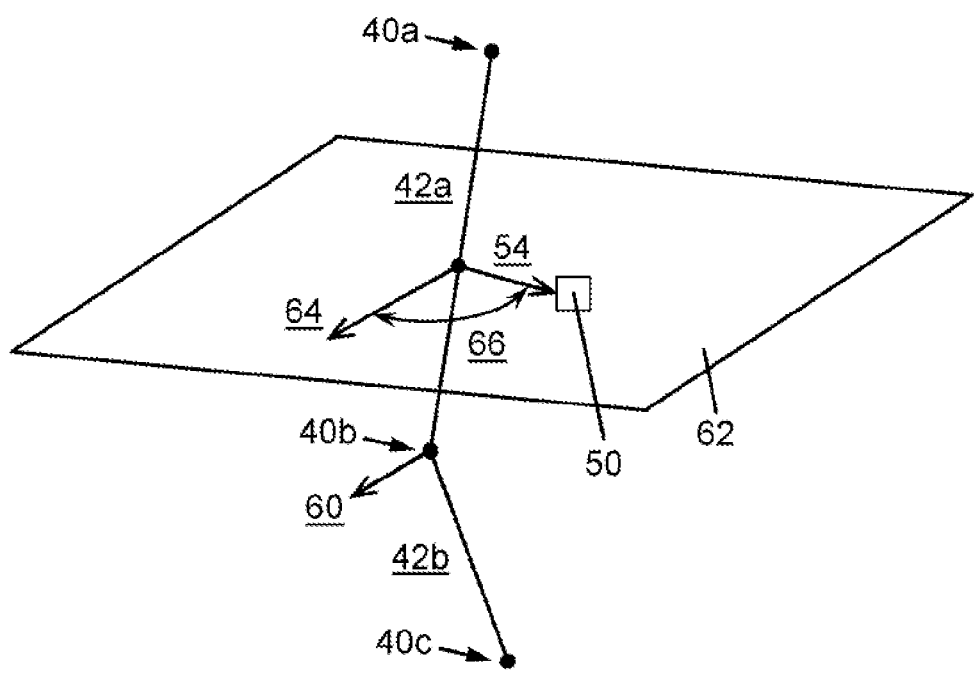
FIG. 5 diagrammatically shows an exemplary angle computation in accordance with embodiments.

FIG. 5 diagrammatically shows an exemplary angle computation in accordance with embodiments.

First positions 40*a*-40*c* have been provided by a computing device of a motion tracking system in accordance with embodiments, the first positions 40*a*-40*c* corresponding to joints such as right hip, right knee and right ankle, and the body member segments 42*a*, 42*b* defined by said first positions correspond to right thigh and right shank. A second position 50 has been provided by the computing device, and said second position 50 corresponds to a tracker positioned on the right thigh of the user of the motion tracking system.

The computing device provides a plane 62 such that a normal vector thereof is aligned or is a vector defined by the direction of the body member segment 42*a*, namely, a vector extending from the hip's first position 40*a* to the knee's first position 40*b* (or vice versa). The plane 62 is furthermore provided such that it contains the second position 50. A tracker vector 54 is defined from the intersection of the body member segment 42*a* and the plane 62, and the second position 50 (which is that of the light emitter of the tracker as registered in the image).

For the calculation of the angle 66, an orientation vector 60 is provided by the computing device. The orientation vector 60 in this example represents an orientation of the knee joint, which is a joint connected to the body member where the tracker is. In other examples, the orientation vector 60 is an orientation of the body member where the tracker is (in this case, that would be the orientation of the right thigh), or an orientation of a predetermined body member (for example, the orientation of the chest or the orientation of the right foot).

The orientation vector 60 is projected onto the plane 62, thereby providing the projected vector 64. The computing device then computes the angle 66 ranging from the projected vector 64 to the tracker vector 54, in one direction or the other depending on how it is previously set in the predetermined configuration of tracker positions so as to avoid incorrect assessment of angles due to a missing negative sign.

Although in the present disclosure several examples have been described with reference to e.g. thighs, shanks, upper arms, lower arms, etc., it will be noted that other body members are also within the scope of the disclosure since the aspects described are likewise applicable to other body members.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for assessing a position of at least one tracker on a subject, the method comprising:
   (a) determining a target configuration of a position of the at least one tracker on the subject;
   (b) activating a light emitter of the at least one tracker and imaging the subject using an optical sensing device to acquire at least one image of the subject comprising an image of the at least one tracker;
   (c) automatically processing the at least one image by a computing device to determine a difference between an actual position of the at least one tracker and the determined target configuration of the position of the at least one tracker; and
   (d) providing an indication of the determined difference to a user of the computing device.

2. The method of claim 1, wherein the at least one tracker comprises a plurality of trackers.

3. The method of claim 2, wherein the indication of (d) comprises an alert that at least one tracker of the plurality of trackers is incorrectly positioned.

4. The method of claim 3, wherein the indication of (d) further comprises user guidance on how to reposition the at least one incorrectly positioned tracker.

5. The method of claim 4, wherein the guidance on how to reposition the at least one incorrectly positioned tracker is determined at least in part by comparing the distances between each of the trackers and the target configuration of (a), and comprises providing instructions to move a closest tracker to a specified tracker position of the target configuration.

6. The method of claim 3, wherein the light emitter of each of the plurality of trackers comprises a plurality of light emission modes corresponding to different emitted light wavelengths.

7. The method of claim 6, wherein the light emitter of each of the plurality of trackers emits light with a color different from a color of the light of the light emitters of other trackers of the plurality.

8. The method of claim 7, wherein determination of (c) is based at least in part on the color of the light of the light emitter of the tracker.

9. The method of claim 2, further comprising automatically determining an identity of the body member upon which each tracker of the plurality of trackers is positioned.

10. The method of claim 2, wherein each of the plurality of trackers comprises at least one antenna configured to transmit and/or receive a wireless signal, and at least one inertial sensor.

11. The method of claim 10, wherein the determining the difference of (c) comprises computing an angle between the at least one inertial sensor and a reference point on the body of the subject.

12. The method of claim 11, wherein the target configuration of (a) comprises a target rotational orientation of the tracker with respect to a reference point on the body of the subject.

13. The method of claim 1, wherein the activating of (b) comprises transmitting a wireless signal to the at least one tracker to trigger activation of the light emitter.

14. The method of claim 1, wherein the determined target configuration of (a) and the actual position of (c) comprise a position of the at least one tracker relative to a position of a readily determinable reference point of a body member of the subject.

15. The method of claim 1, further comprising repeatedly performing (b)-(d).

16. The method of claim 15, wherein (b)-(d) are repeated until the determined difference of (c) is less than a threshold value.

17. The method of claim 16, wherein when the determined difference of (c) is less than the threshold value, the indication of (d) comprises an indication that the one or more tracker is in the predetermined position.

18. The method of claim 17, wherein the target configuration of (a) comprises a target rotational orientation of the tracker with respect to a reference point on the body of the subject, and the determined difference of (c) comprises an angular difference between the orientation of the one or more trackers and the target rotational orientation.

19. A positioning system for properly positioning at least one tracker on a body of a subject, the positioning system comprising:
   at least one tracker adapted to be arranged on the body of the subject, the at least one trackers comprising: a light emitter, at least one antenna configured to transmit and/or receive a wireless signal, and at least one inertial sensor;
   an optical sensing device; and
   a computing device comprising at least one antenna configured to transmit and/or receive a wireless signal, the computing device being configured to:
      (a) determine a target configuration of a position of the at least one tracker on the subject;
      (b) activate a light emitter of the at least one tracker and image the subject using the optical sensing device to acquire at least one image of the subject comprising an image of the at least one tracker;
      (c) automatically process the at least one image to determine a difference between an actual position of the at least one tracker and the determined target configuration of the position of the at least one tracker; and
      (d) provide an indication of the determined difference to a user of the positioning system.

20. The positioning system of claim 19, the at least one tracker comprises a plurality of trackers, each comprising at least one antenna configured to transmit and/or receive a wireless signal, and at least one inertial sensor.

* * * * *